United States Patent [19]

Ericsson

[11] 4,009,260

[45] Feb. 22, 1977

[54] FRACTIONATION OF SPERM

[75] Inventor: Ronald J. Ericsson, Sausalito, Calif.

[73] Assignee: Schering Aktiengesellschaft, Berlin & Bergkamen, Germany

[22] Filed: Dec. 11, 1974

[21] Appl. No.: 531,728

Related U.S. Application Data

[63] Continuation-in-part of Ser. No. 391,471, Aug. 24, 1973, abandoned.

[30] Foreign Application Priority Data

Apr. 19, 1973 Germany ..................... 2321000

[52] U.S. Cl. .............................. 424/105; 195/1.8
[51] Int. Cl.$^2$ ................... A61K 35/52; C12K 9/00
[58] Field of Search ................. 195/1.8; 424/105

[56] References Cited

UNITED STATES PATENTS 3,687,806   8/1972   Bovenkamp .................. 195/1.8

OTHER PUBLICATIONS

S.W.B. Research Corp. —Chem. Abst., vol. 66 (1967) p. 44818q.
Shilling—J. Reprod. Fert., vol. 11 (1966) pp. 469–472.
Ericsson et al.—Nature, vol. 246, Dec. 1973 pp. 421–424.
Population Reports—Series I, No. 2 (May, 1975) pp. 25, 29 and 31.

Primary Examiner—Sam Rosen
Attorney, Agent, or Firm—Millen & White

[57] ABSTRACT

Motile sperm are separated from immotile and abnormal sperm of mammalian semen by maintaining, at a temperature at which the motile sperm are motile, a layer of at least the sperm portion of the semen in interfacial contact with a discrete lower layer of an aqueous contacting medium physiologically acceptable to the sperm in which the motile sperm have a lower migration rate than in the upper layer, until the motile sperm of the semen have migrated at a preferential rate to the contacting medium, thereby providing a sperm fraction consisting essentially of normal motile sperm with enhanced Y-sperm content. Repeating the process with a second contacting medium physiologically acceptable to the sperm which further retards the migration rate of the motile sperm increases substantially the Y- to X-sperm ratio of the sperms which migrate thereto. The resulting sperm fraction, because of its enhanced Y-sperm content, can be used for artificial insemination to increase the incidence of male offspring. The first step alone can be used to improve the quality of semen having an abnormally low normal motile sperm content, thereby increasing the chances of a successful insemination.

37 Claims, No Drawings

FRACTIONATION OF SPERM

BACKGROUND OF THE INVENTION

This is a continuation-in-part of application Ser. No. 391,471, filed Aug. 24, 1973 now abandoned.

This invention relates to methods for increasing the incidence of males in the offspring of mammals and for increasing the frequency of fertilization rate thereof by artificial insemination, to processes for increasing the ratio of Y-sperm to X-sperm and for increasing the ratio of motile sperm to immotile sperm in mammalian semen and to kits for conducting the process.

In mammals, the sex is determined by two different types of sperm, which have either an X-chromosome (X-sperm) or Y-chromosome (Y-sperm). Fertilization with Y-sperm produces males. The assumption that these two kinds of sperm differ in size and weight has led to a series of investigations, in which the separation of the X- and Y-sperm has been attempted by sedimentation, centrifuging, electrophoresis, variation in pH-value or flotation. See, e.g., U.S. Pat. No. 3,687,806; Shilling, Erich, J. Reprod. Fert. (1966) 11, 469–472; Chem. Abstr. 66, 44818q (1967); A. M. Roberts, Nature, Vol. 238, pp. 223–275 (1972). Lang, J. L., Chemtech, March, 1973, page 190–192; Symposium, "Sex Ratio at Birth - Prospects for Control," American Soc. of Animal Sci., July 31 - Aug. 1, 1970; Beatty, R. A., Bibliography (With Review) Reproduction Research Information Service, Ltd., Biblphy. Reprod. 23:1, Jan. 1974.

The importance of a method of separating Y-sperm from the sperm of mammals is obvious. For example, by the separation of Y-sperm from semen, it would be possible for an animal breeder to increase the incidence of male offspring in the animals by artificially inseminating the animals with sperm containing a high proportion of Y-sperm. In breeding cattle and sheep, where meat production is of importance, insemination with Y-sperm would be valuable. Because the males during any given growth period (for example the period up to weaning) are generally heavier than females of the same age and where meat production is of primary importance to the breeders, artificial insemination with only or predominantly Y-sperm would be of particular value.

Such a method would also be of great importance to humans. The desire for a child of a particular sex often is one of the reasons for families with a large number of children. A method of separting X- and Y-sperm would considerably facilitate family planning, with resulting reduction in population and the problems connected therewith.

In cases of marginally fertile human semen, and with stored semen, the percentage of motile sperm therein is abnormally low. The presence, along with normal motile sperm, of high percentages of immotile sperm, defective sperm, dead sperm and their decomposition products, and other non-sperm components of semen, has an adverse effect upon the normal motile sperm. It would be desirable if the quality of such semen, viz., the ratio of normal motile sperm to immotile sperm, could be improved, thereby increasing the likelihood of successful impregnation. Also, a sample of motile sperm having a low proportion of immotile sperm and other semen components can more safely be introduced directly into the uterus, thus further increasing the chances of a successful insemination.

Accordingly, it is an object of the present invention to provide a novel process for the production of sperm fractions from mammalian semen having enhanced Y-sperm content. Another object is the provision of a process for separating motile sperm from immotile sperm. Another object is the provision of a kit for conducting such processes. Another object is the provision of sperm fractions of enhanced motile sperm content. Still another object is the provision of sperm fraction consisting predominantly, i.e., at least 65%, preferably at least 80%, and most preferably at least 90%, of Y-sperm. A further object is the provision of a method for artificially inseminating mammals employing such sperm fractions. A still further object is the method of artificially inseminating mammals in a manner which increases the incidence of male offspring. Other objects will be apparent to those skilled in the art to which this invention pertains.

SUMMARY OF THE INVENTION

According to this invention, the motile sperm are separated from the motile sperm of mammalian semen by maintaining at least the sperm portion of progressively motile sperm-containing semen, either as such or preferably as a suspension in an aqueous vehicle physiologically acceptable to the sperm, as an upper layer in vertical interfacial contact with a discrete lower layer of an aqueous contacting medium physiologically acceptable to the sperm in which the motile sperm has a lower migration rate than in the upper layer, until motile sperm of the semen have migrated into the contacting medium, thereby providing a contacting medium containing a sperm fraction having a higher proportion of motile sperm with enhanced Y-sperm content. Repeating the process with the thus-obtained sperm fraction and a second contacting medium in which the motile sperm have a still lower migration rate than in the first contacting medium, produces a sperm fraction consisting predominantly of motile Y-sperm.

Motile sperm is separated from immotile sperm in the first fractionation, thereby providing a highly motile sperm fraction of enhanced content of motile Y-sperm and normal morphology. Sperm fractions obtained by subsequent fractionations have greatly enhanced Y-sperm contents. The thus-produced motile sperm fractions, usually after being isolated from the contacting medium, can be used in a conventional manner for artificial insemination purposes.

DETAILED DISCUSSION

This invention in its various aspects is based upon two discoveries. In its semen quality improving aspect, this invention is based upon the discovery that the motile sperm content of semen having an abnormally low normal motile sperm content, can be selectively fractionated therefrom according to the fractionation process of this invention, in high yield to produce a high quality sperm fraction having a substantially enhanced motile sperm content and a greatly reduced content of immotile sperm, morphologically and genetically abnormal sperm, dead sperm and their decomposition products and nonsperm semen components, e.g., round cells, particulate material, etc. In its Y-sperm enhancing aspect, this invention is based upon the discovery that according to the multiple fraction process of this invention, sperm can be fractionated to produce motile sperm fractions consisting predominantly of normal Y-sperm. See A. M. Roberts, supra, for a discussion of migration rates of motile sperm.

Whereas motile and immotile sperm suspended in e.g., isotonic saline or Tyrode solution, both settle downwardly therein at substantially the same rate, if a suspension of semen containing progressively motile sperm in a suspending vehicle which does not substantially retard downward migration rate is vertically layered on top of a discrete lower layer of a contacting medium which does retard the migration rate of the semen, the motile sperm will migrate downwardly through the contacting medium, leaving most or all of the immotile and morphologically abnormal sperm and other non-sperm semen components behind.

In this aspect of this invention, the proportion of motile sperm can be increased from 70% or far less, in the case of marginally fertile or stored sperm, to 90–95% or higher. Moreover, whereas semen contains about equal amounts of X- and Y-sperm, the Y-sperm content of the sperm in the contacting medium is also increased, e.g., to about 55–65%, in this aspect of the process of this invention.

In another aspect of this invention, the fractionation is repeated with the thus-obtained sperm fraction and a second contacting medium which retards migration rate more than the first contacting medium, which further enhances the Y-sperm content of the sperm migrating thereto, so that sperm fractions having a 70–90% or more Y-sperm content can be obtained.

It will be appreciated that enhancing the motile sperm content of the thus-obtained sperm fractions causes a corresponding decrease in total number of sperm recovered, both from the reduction in immotile sperm content and from the loss of the motile sperm which have not yet migrated into the contacting medium when the process is terminated. However, the recovery of total motile sperm is surprisingly high. The loss of motile sperm is compensated for by the improved quality of the resulting sperm sample, since the chances of a successful impregnation therewith are greater than a starting sample of poorer quality semen having a higher total sperm count. Finally, because of the high quality of the resulting sperm sample, impregnation directly into the human uterus is clinically more acceptable, thereby further increasing the chances of fertilization.

The process of the invention can be used with the semen of all mammals. Of special interest is the semen of animals which are used in agriculture or for other economic purposes, for example, horses, cattle, pigs, sheep, goats, rabbits, etc. The process can also be used in the same manner with human semen, both in cases of marginal sperm fertility and when a male child is desired.

The starting sperm from which the motile sperm are fractionated are preferably and ordinarily dispersed in a vehicle physiologically acceptable to the sperm. Such a vehicle is nontoxic to the sperm and does not weaken the fertility of the sperm, i.e., it must neither harm nor destroy the sperm. Such a vehicle has a pH-value within the range of about 6 to 8 which is compatible with the semen and an osmotic pressure at which the sperm are not compressed or disintegrated.

Because the separation process involves the migration of motile sperm into an aqueous contacting medium which retards the sperm migration rate, the aqueous vehicle in which the sperm are suspended in the initial fractionation step ordinarily should not significantly retard the sperm migration rate, in order to avoid interfering with the migration of the motile sperm from the suspending vehicle into the contacting medium. Such vehicles have a density close to that of water, i.e., about 1.001 to 1.100 g/ml., preferably about 1.005 to 1.070 g/ml. Preferably such solutions also have a low viscosity, viz., about that of water. However, the fractionation aspect of the process of this invention is based upon the use of a contacting medium as a lower layer in which the motile sperm migrate at a slower rate than the rate at which they migrate in the upper layer, i.e., the process is based upon a migration rate differential between the upper and lower layers. Therefore, while it is preferable that the suspending vehicle be one which does not retard the migration of motile sperm, because higher recoveries of motile sperm are achieved with such suspending vehicles, those which do retard migration rates can be used as long as the contacting medium retards the migration rate even more so. Moreover, in one aspect of the multiple fractionation process of this invention, the first contacting medium acts as a suspending vehicle and is layered above a second contacting medium.

Thus, it is possible to employ whole semen in the upper layer, either as such or diluted with a physiologically acceptable suspending vehicle. However, because whole semen is viscous even when diluted, the contacting medium must be correspondingly more viscous to provide the required retardation of downward migration rate of the motile sperm. As a consequence, lower recoveries of the motile sperm present in the semen are realized. Therefore, it is preferably to separate the sperm from the seminal fluid, usually after dilution with a physiologically acceptable suspending vehicle, e.g., by centrifugation, and re-suspend the sperm in fresh suspending vehicle before conducting the fractionation process.

Examples of aqueous solutions which are physiologically acceptable to the sperm and can thus be used as suspending vehicles and contacting media are well known in the art and include solutions such as for example, Tyrode solution, Ringer solution, Hanks' solution, isotonic sodium chloride solutions, Medium 199, Eagle's Medium, etc. The density and/or viscosity of these solutions can be increased by the addition thereto of an additive described hereinafter which can be present in the contacting medium.

The contacting medium can be entirely different in composition from the aqueous suspending vehicle, so long as both are physiologically acceptable to the sperm. However, they can be and preferably are essentially the same solutions, e.g., Tyrode solution, with the contacting medium containing an additional ingredient or a larger amount of a common ingredient, which retards significantly the migration rate of the motile sperm compared to their settling rate in the suspending vehicle. As stated above, such an ingredient ordinarily increases both the density and the viscosity of the contacting medium.

Aqueous contacting media which retard the migration rate of motile semen compared to the suspending vehicle generally have significantly higher densities and viscosities than water, isotonic saline solutions, Tyrode solution and other solutions suitable as suspending vehicles. It is theoretically possible to increase the density of the contacting medium without simultaneously significantly increasing its viscosity. Similarly, polymers which form a sol or gel can greatly increase viscosity and have little effect upon density. However, as a practical matter a contacting medium which retards migration rate and is physiologically acceptable to the sperm generally has both higher density and viscosity than a suspending vehicle which does not retard migration rate. In any event, whether the lowering of the migration rate of the motile sperm in the contacting medium is the result of the latter's higher density, higher viscosity, or both, is not critical as long as the migration rate of the motile sperm is reduced.

As stated above, the contacting medium, in addition to retarding the migration rate of the sperm, should meet the criteria mentioned above for the suspending vehicle of low density in which the sperm may be dispersed, i.e., it must be physiologically acceptable to the sperm. Thus, there may be employed any physiologically acceptable solution in which sperm can be maintained in a viable and motile state, for example, those mentioned above as suspending vehicles, which are adapted by means of soluble materials known to pharmacologists and physiologists to the desired condition of higher density and/or viscosity. Such additives include, for example, salts, low molecular and high molecular weight organic compounds, e.g., mon- and oligo-saccharides, aminoacids, peptides, proteins, proteids and synthetic polymers, for example, polyvinylpyrrolidone.

Specific examples of such soluble materials are:
PROTEINS
Albumins
 Bovine Serum Albumin (3–25%) Density: 1.012–1.075 g/ml
 Human Serum Albumin
 Ovalbumin (6–15%) Density: 1.018–1.041

| Globulins | |
|---|---|
| Alpha Bovine Globulin (10%) Density (1.028) | |
| Human and other alpha globulins | |
| Beta Globulins | Thrombin |
| Gamma Globulins | Hemoglobin |
| Glyco proteins | Casein |
| Fibrinogen | Lactoglobulins |
| Prothrombin | Lactalbumins |

| AMINO ACIDS | PEPTIDES | SACCHARIDES |
|---|---|---|
| Alanine | L-Alanyl-L-Aline | Monosaccharides |
| Arginine | L-Alanyl-L-Lysine | Glucose |
| Cysteine | L-Alanyl-L-Serine | Fructose |
| Glutamic Acid | Tri-L-Alanine | Disaccharides |
| Glycine | Hexa-L-Alanine | Maltose |
| Histidine | Glycyl-Glycine | Lactose |
| Hydroxyproline | Glycyl-L-Leucine | Sucrose |
| Leucine | L-Leucyl-L-Alanine | Polysaccharides |
| Lysine | L-Phenylalanyl-Glycine | Dextrans |
| Methionine | L-Seryl-Glycine | |
| Ornithine | L-Tyrosyl-L-Alanine | SALTS |
| Phenylalanine | | NaCl |
| Proline | | KCl |
| Serine | | MgCl |
| Tryptophan | | CaCl |
| Tyrosine | | $NaH_2PO_3$ |
| Valine | | $NaHCO_3$ |

An additive employed for achieving the desired retardation of sperm migration rate need not be completely soluble in the starting solution. Thus, high molecular weight proteins and synthetic polymers can be employed as a colloidal sol or gel.

Migration rate differential required to achieve the desired separation of motile sperms from immotile sperms and to fractionate Y-sperms from semen is not critical and partially depends on the nature and quality of the mammal semen used and the additives present in the contacting medium to provide a density and/or viscosity differential between the upper and lower layers. For example, when using bovine serum albumin or other serum albumin or serum globulin protein, and a suspending vehicle which does not retard downward migration, the protein need be present in the contacting medium at a concentration of only about 1–5%, preferably about 3–5%, to achieve separation of motile sperm from immotile sperm. However, to achieve optimum separation of motile Y-sperm from motile X-sperm, the protein should be present at a higher concentration in the final contacting medium, e.g., 3–50%, preferably about 10–25%.

The starting sperm which are preferably dispersed in a suspending vehicle and separated from seminal fluid, can be brought into contact with the contacting medium in any desired manner, so long as care is taken that mixing of the semen layer with the layer of contacting medium does not occur. The preferred method of contacting is to overlay the contacting medium with the semen layer. However, it is also possible, with sufficient care, to underlay the semen layer with a layer of the contacting medium. When the semen, optionally dispersed in a suspending vehicle, is brought into contact with the contacting medium, a single contact leads to satisfactory separation of motile from immotile sperm and significant enhancement of the Y-sperm content of the fractionated motile sperm. However, the extent of Y-sperm content enhancement can be and preferably is increased by repeating the contacting step one or more times, i.e., contacting the sperm fraction which migrated to the first contacting medium with a second contacting medium in which the sperm have a lower migration rate than in the first contacting medium, i.e., one having a higher density (and/or viscosity).

When the sperm fractionation is repeated by unerlayering the first contacting medium with a second contacting medium, the latter should be a solution which further retards the sperm migration rate, i.e., a solution in which the motile sperm migrate at a lower rate than the rate at which they migrate in the first contacting medium.

The repeated contacting step can be carried out with a single contacting medium or with a plurality, for example, two or three, of contacting media of progressively higher density and/or viscosity, for example, by underlaying the dispersed starting sperm with the first contacting medium of higher density and then underlaying this solution with the second contacting medium.

The repeated contacting step can alternatively be carried out by first separating the sperm which have migrated to the contacting medium therefrom and contacting the separated semen, resuspended in fresh suspending vehicle, with the second contacting medium in the same manner as in the first contacting step. A still further alternative is to separate the first contacting medium containing the separated sperm from the upper starting sperm layer and thereafter contacting the separated first contacting medium with a lower layer of second contacting medium.

For convenience, the process is usually conducted at room temperature but can be conducted at any higher or lower temperature at which the sperm can be maintained alive and motile, e.g., from about 15° C. to about the normal body temperature of the species of mammal whose sperm is being fractionated, viz., up to about 40° C., preferably about 20°–25° C. At elevated temperatures or when conducting the process for several hours, it is sometimes advantageous to incorporate into the suspending vehicle and contacting medium an antibiotic, e.g., tetracycline, a penicillin or gentamycin, or a bacteriostat which is physiologically acceptable to the semen.

The time required for carrying out the isolation (or separation) depends on the species of mammal, the nature of the contacting medium and the type of isolation or separation used, the exact time not being critical. Very short times give poor motile sperm recoveries. Generally, contact times of 0.25–10.0, preferably 1.0–4.0 hours, are employed. A contact period of about 0.5 to 10 hours and preferably about 1 to 3 hours generally is sufficient to separate a high proportion of the motile sperm from the immotile sperm and substantially increase the Y-sperm content of the motile sperm which have migrated to the contacting medium.

The sperm in the final contacting medium can be recovered for artificial insemination by separating all, or, if a lower recovery of motile sperm can be tolerated, the lower fraction only of the final contacting medium, e.g., by carefully pipetting or decanting. The contacting medium containing the fractionated sperm can be used as such for insemination purposes if the vehicle is suitable for such purpose, diluted to render it suitable for that purpose, or the sperm can be separated therefrom in a conventional manner, e.g., by centrifugation, and then resuspended for use in a suspending vehicle physiologically acceptable to the sperm and suitable as a vehicle for insemination purposes, e.g., Tyrodes solution.

The sperm fractionation process of this invention can be carried out in vessels of any form, such as are customarily used by those skilled in the art for working with small quantities of fluids, for example, burettes, pipettes, separating tubes and columns having a suitable closure, etc. As any vertical elongate vessel is operable, conventional forms of constructions can be employed which may be modified as desired.

The necessary working materials are advantageously provided in the form of a set of accessories, which is preferably a single use, throw-away package, to the practitioner who intends to inseminate with the fractionated sperm. Such a set of accessories preferably contains the following individual constituents, which have already been described, in suitable preferably sterile containers:

a. a vessel for working with small quantities of fluids;

b. a physiologically acceptable aqueous suspending vehicle for suspending the sperm, such as has been described above, and c. a physiologically acceptable aqueous contacting medium for contacting the sperm-containing suspending vehicles. As the contacting medium can generally be prepared from the suspending vehicle, or vice versa, alternatively, the set of accessories can contain as constituent (c) an ingredient to add to a portion of (b) to convert it into a contacting medium, or can contain as constituent (b) an aqueous solution to add to a portion of (b) to convert it into a suspending vehicle. The kit optionally can also contain d. an insemination syringe, such as is generally known to those skilled in the art, and optionally also, e. instructions for operation.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following Examples, the temperatures are set forth at room temperature and uncorrected in degrees Celsius unless otherwise indicated, all parts and percentages are by weight. The values obtained in elemental analyses are within commonly accepted limits of error.

Before separation, the number and motility of the sperm is determined according to the procedure of C. Schirren (Praktische Andrologie, Verlag Bruder Hartmann, Berlin 1971). The subsequent isolation (or separation) is followed by determining X- and Y-sperm contents according to the quinacridine technique Acta biol. med. germ. 28 (1972) 189–92. The sperm can be recovered by centrifuging.

The fractionation vessels used in the following examples were vertically positioned 10 cm lengths of 5 mm internal diameter glass tubing flame sealed at their bottom ends. In those of Examples 1–12 employing Tyrode solutions containing 6% and 15% BSA, the bottom 15% BSA layer (0.4 ml) was 16 mm in height; the middle 6% BSA layer (0.8 ml) was 32 mm in height and the top starting sperm layer (0.5 ml) was 20 mm in height. In those examples using 10%, 15% and 25% BSA solutions, 0.3 ml of each were used to give three 12 mm layers positioned below a 20 mm layer (0.5 ml) of starting sperm. In Examples 13 and 14, the 15% BSA solution (0.5 ml) was 20 mm in height, the 6% solution (0.1 ml) positioned above it was 40 mm in height and the upper sperm layer (0.5 ml) was 20 mm in height.

The contact times were determined by the rate at which the motile sperm migrated through the various contacting media. Normal motile sperm migrates rapidly downwardly at room temperature through vehicles which do not retard migration rate, e.g., at about 30–50 cm per hour. In 6% BSA, the migration rate is about one-tenth that, e.g., about 4–5 cm per hour. Generally speaking, contacting media are employed which lower migration rates to 1–50%, preferably about 5–25%, of the unretarded migration rate of the motile sperm employed. When Y-sperm and X-sperm fractionation is desired, contacting times are selected which permit a portion only, e.g., from 5–75%, preferably 10–50%, of the motile sperm above the contacting medium to migrate thereto. As would be obvious, if the contact time is long enough to permit all or substantially all of the motile sperm to migrate into the contacting medium below the sperm layer, significant Y-sperm and X-sperm fractionation will not occur unless the lower portion of the contacting medium is separated from the upper portion thereof before all of the motile sperm have migrated to the bottom of the contacting medium. In the motile-immotile sperm fractionation process aspect of this invention, where Y- and X-sperm fractionation is not sought and maximum motile sperm recovery is desired, contacting times long enough to achieve more than 75% motile sperm recovery can be advantageously employed. The only limiting factors are the life span of the motile sperm in the contacting medium and the settling rate of the immotile sperm downwardly into the contacting medium which is about one-tenth the migration rate of motile sperm therein. When a plurality of contacting medium are employed, few immotile sperm penetrate the last contacting medium.

In the examples below, the abbreviations have the following meanings:

| IM: | % Initial motility | R: | % recovered |
| --- | --- | --- | --- |
| FM: | % Final motility | M: | % Motility of the sperm |
| | | Y: | % Y sperm |

EXAMPLE 1 a. Fresh human semen is mixed in a 1:1 ratio with Tyrode solution and, in order to separate the sperm from the other constituents of the semen, the mixture is centrifuged. After determining the motility and number of sperm, $50 \times 10^6$ sperm are re-suspended in 0.5 ml. of Tyrode solution (density = 1.005 g/ml). Simultaneously a Tyrode solution having a pH-value of 7.4 to 7.6 is adjusted with bovine serum albumin (BSA) to a 6% concentration (density = 1.021 g/ml). The sperm-containing Tyrode solution is layered over 0.9 ml. of the BSA solution in a sealed Pasteur pipette. After one hour the supernatant Tyrode solution and the BSA solution are separated from each other. The sperm are recovered from the Tyrode-solution and the BSA-solution, and their number and motility and also the content of X- and Y-sperm are determined. The results are summarized below:

Tyrode solution: IM = 70, FM = 25;
6% BSA-Tyrode solution: R = 30, M = 90–95, Y = 63–67.

b. $50 \times 10^6$ of the sperm obtained as described in Example 1a), containing 63–67% of the Y-sperm, are suspended in 0.5 ml. of Tyrode solution, and the latter is layered over 0.9 ml. of a 10% BSA solution (density = 1.033 g/ml). After one hour the supernatant Tyrode solution and the BSA solution are separated from each other. The sperm are recovered from the Tyrode-solution and the BSA solution, and their number and motility and also the X- and Y-sperm contents are determined. The results are summarized below:

Tyrode solution: IM = 90, FM = 40–60;
10% BSA-Tyrode solution: R = 40, M = 95, Y = 73–78.

EXAMPLE 2

Fresh human semen is mixed with Tyrode solution in a 1:1 ratio. The mixture is centrifuged to separate the sperm. After determining the motility and number of the sperm, $50 \times 10^6$ sperm are re-suspended in 0.5 ml. of Tyrode solution and the latter is layered over 0.8 ml. of a 6% BSA solution which has previously been layered over 0.4 ml. of a 15% BSA solution (density = 1.047 g/ml). After one and a half hours the respective solutions are separated from each other. The sperm are recovered from the two BSA-solutions, and their number and motility and also their X- and Y-sperm contents are determined. The results are summarized below:

Tyrode solution: IM = 70, FM = 25;
6% BSA solution: R = 20, M = 90–95, Y = 60–65;
15% BSA solution: R = 10, M = 95, Y = 78–80.

EXAMPLE 3 a. Fresh human semen is mixed with Tyrode solution in a 1:1 ratio. The mixture is centrifuged to separate the sperm. After determining the motility and number of sperm, $50 \times 10^6$ sperm are re-suspended in 0.5 ml. of Tyrode solution and the latter is layered over 0.9 ml. of a 6% BSA solution. After one hour, the supernatant Tyrode solution and the BSA solution are separated from each other. The sperm are recovered from the BSA solution, and their number and motility and also the content of X- and Y-sperm are determined. The results are summarized below:

Tyrode solution: IM = 70, FM = 25;
6% BSA solution: R = 30, M = 90–95, Y = 63–67.

b. $50 \times 10^6$ sperm obtained as described in Example 3a), containing 63–67% of Y-sperm, are suspended in 0.5 ml. of Tyrode solution, and the latter is layered over 0.9 ml. of a 10% BSA solution. After one hour the supernatant Tyrode solution and the BSA solution are separated from each other. The sperm are recovered from the BSA solution, and their number and motility and also the X- and Y-sperm contents are determined. The results are summarized below:

Tyrode solution: IM = 90, FM = 45–60;
10% BSA solution: R = 45–50, M = 95–98, Y = 74–78.

c. $50 \times 10^6$ sperm obtained as described in Example 3b), containing 74–78% of Y-sperm, are suspended in 0.5 ml. of Tyrode solution, and the latter is underlaid with 0.9 ml. of a 20% BSA solution (density = 1.062 g/ml). After one hour the supernatant Tyrode solution and the BSA solution are separated from each other. The sperm are recovered from the BSA solution, and their number and motility and also the content of X- and Y-sperm are determined. The results are summarized below:

Tyrode solution: IM = 95, FM = 92;
20% BSA solution: R = 43, M = 97, Y = 85.

Comparable results are obtained with each of bovine, equine, porcine and ovine sperm.

EXAMPLE 4 a. Fresh human semen is mixed with Tyrode solution in a 1:1 ratio and the sperm are separated by centrifuging. After determining the motility and number of sperm, $50 \times 10^6$ sperm are re-suspended in 0.5 ml. of Tyrode solution and the latter is layered over 0.9 ml. of a 3% BSA solution (density = 1.012 g/ml). After one hour the supernatant Tyrode solution and the BSA solution are separated from each other. The sperm are recovered from the BSA solution, and their number and motility and also the content of X- and Y-sperm are determined. The results are summarized below. There is achieved essentially only a separation of motile from immotile sperm.

Tyrode solution: IM = 65, FM = 25;
3% BSA solution: R = 30–45, M = 85–90, Y = 57.

EXAMPLE 5

Fresh human semen is mixed with Tyrode solution in 1:1 ratio and the sperm are separated by centrifuging. After determining the motility and number of sperm, $50 \times 10^6$ sperm are re-suspended in 0.5 ml. of Tyrode solution and the latter is layered over 0.3 ml. of a 10% BSA solution, which has been layered over 0.3 ml. of a 15% BSA solution, which has been layered over 0.3 ml. of a 25% BSA solution (density = 1.075 g/ml). After one hour the upper layer (Tyrode solution) is separated. After one and a half hours the second layer (10% BSA) is separated. After two hours the residual solutions (15% and 25% BSA) are separated. The sperm are recovered from the respective BSA solutions and their number and motility and also the X- and Y-sperm contents are determined. The results are summarized below:

Tyrode solution: IM = 65, FM = 20;
10% BSA solution: R = 10–15, M = 50–60, Y = 55–60;
15% BSA solution: R = 10, M = 75–85, Y = 60–70;
25% BSA solution: R = 10, M = 95, Y = 75.

EXAMPLE 6 a. Fresh rabbit-semen is mixed with Tyrode solution in a 1:1 ratio and the mixture is centrifuged to separate the sperm from the other constituents of the semen. After determining the motility and number of sperm, $50 \times 10^6$ sperm are re-suspended in 0.5 ml. of Tyrode solution having a pH value of 7.6. Simultaneously, a Tyrode solution having a pH value of 7.6 is adjusted with bovine serum albumin (BSA) to a BSA-concentration of 6% of BSA (density = 1.021 g/ml). The sperm-containing Tyrode solution is layered over 0.9 ml. of a BSA solution in a sealed Pasteur pipette. After one hour, the supernatant Tyrode solution and the BSA solution are separated from each other. The sperm are recovered from the BSA solution, and their number and motility are determined. The results are summarized below:

Tyrode solution: IM = 75, FM = 75;
6% BSA-Tyrode solution: R = 26, M = 95.

b. $50 \times 10^6$ sperm obtained as described in Example 6a) are suspended in 0.5 ml. of Tyrode solution, and the latter is layered over 0.9 ml. of a 10% BSA solution. After one hour the supernatant Tyrode solution and the BSA solution are separated from each other. The sperm are recovered from the BSA solution, and their number and motility are determined. The results are summarized below:

Tyrode solution: IM = 95, FM = 80;
10% BSA solution: R = 30–40, M = 75.

Fertilization experiments resulted in preponderantly male foetuses, i.e., a sufficient separation of the Y-sperm from the X-sperm had been achieved to produce a preponderance of male offspring.

EXAMPLE 7

Fresh rabbit semen is mixed with Tyrode solution in a 1:1 ratio, and the mixture is centrifuged to separate the sperm. After determining the motility and number of sperm, $100 \times 10^6$ sperm are re-suspended in 0.5 ml. of Tyrode solution and the latter is layered over 0.8 ml. of a 6% BSA solution. The 6% BSA solution is layered over 0.4 ml. of a 15% BSA solution. After one hour the upper layer is separated off. After one and a half hours, the residual solutions are separated. The sperm are separately recovered from the BSA solutions, and their number and motility are determined. The results are summarized below:

Tyrode solution: IM = 75, FM = 70;
6% BSA solution: R = 10, M = 90;
15% BSA solution: R = 5, M = 98.

EXAMPLE 8

Fresh human semen is mixed in a 1:1 ratio with Tyrode solution and the mixture is centrifuged to separate the sperm from the other constituents of the semen. After determining the motility and number of sperm, $50 \times 10^6$ sperm are re-suspended in 0.5 ml. of Tyrode solution at a pH value of 7.6. Simultaneously, a Tyrode solution is adjusted with ovalbumin (OVA) to 10% OVA-concentration (density = 1.028 g/ml) and a pH value of 7.3–7.4. The sperm-containing Tyrode solution is layered over 0.9 ml. of OVA-solution in a sealed Pasteur pipette. After one hour the supernatant Tyrode solution and the OVA-solution are separated from each other. The sperm are recovered from the OVA-solution, and their number and motility and also the X- and Y-sperm contents are determined. The results are summarized below:

Tyrode solution: IM = 75–80, FM = 25–30,
10% OVA-solution: R = 25–30, M = 85–90, Y = 62–66.

EXAMPLE 9

Fresh human semen is mixed in a 1:1 ratio with Tyrode solution and the mixture is centrifuged to separate the sperm. After determining the motility and number of sperm, $50 \times 10^6$ sperm are re-suspended in 0.5 ml. of Tyrode solution and the latter is layered over 0.8 ml. of 6% OVA-solution (density = 1.018 g/ml). The 6% OVA-solution is layered over 0.4 ml. of 15% OVA-solution (density = 1.041 g/ml). After one hour, the upper layer is separated off. After one and a half hours the residual solutions are separated. The sperm are recovered from the OVA-solutions and their number and motility and also the X- and Y-sperm contents are determined. The results are summarized below:

Tyrode solution: IM = 80, FM = 45;
6% OVA-solution: R = 15, M = 80–85, Y = 70–73;
15% OVA-solution: R = 3–5, M = 45–50, Y = 60–67.

EXAMPLE 10

Fresh human semen is mixed in the ratio of 1:1 with Tyrode solution and in order to separate the sperm from the other constituents of the semen the mixture is centrifuged. After determining the motility and number of the sperm, $50 \times 10^6$ sperm are re-suspended in 0.5 ml. of Tyrode solution, and the latter is layered over 0.8 ml. of 6% OVA-solution. The 6% OVA-solution is layered over 0.4 ml. of 15% OVA-solution. After one and a half hours the solutions are separated from each other. The sperm are recovered from the OVA-solutions and their number and motility and also X- and Y-sperm contents are determined. The results are summarized below:

Tyrode solution: IM = 65, FM = 20;
6% OVA-solution: R = 30, M = 75, Y = 65–73;
15% OVA-solution: R = 5, M = 80–85, Y = 70–75.

EXAMPLE 11

Fresh human semen is mixed in a 1:1 ratio with Tyrode solution and the mixture is centrifuged to separate the sperm from the other constituents of the semen. After determining the motility and number of sperm, $50 \times 10^6$ sperm are re-suspended in 0.5 ml. of Tyrode solution having a pH value of 7.6. Simultaneously, a Tyrode solution having a pH value of 7.6 is adjusted with alpha-bovine-globulin (BG) to a BG-concentration of 10% of BG (density = 1.028 g/ml). The sperm-containing Tyrode solution is layered over 0.9 ml. of the 10% BG solution in a sealed Pasteur pipette. After one hour the supernatant Tyrode solution and the 10% BG solution are separated from each other. The sperm are recovered from the BG solution and their number and motility and also the X- and Y-sperm contents are determined. The results are summarized below:

Tyrode solution: IM = 20, FM = 25;

BG solution: R = 24, M = 80, Y = 60.

EXAMPLE 12

Fresh rabbit semen is mixed with Tyrode solution in a 1:1 ratio, and the mixture is centrifuged to separate the sperm. After determining the motility and number of sperm, $50 \times 10^6$ sperm are re-suspended in 0.5 ml. of Tyrode solution and the latter is layered over 0.8 ml. of a 10% BSA solution. The 10% BSA solution is layered over 0.4 ml. of a 15% BSA solution. After one hour the upper layer is separated off. After one and a half hours the residual solutions are separated. The sperm are recovered from the BSA solutions and their number and motility are determined. The results are summarized below:

Tyrode solution: IM = 68, FM = 45;
10% BSA solution: R = 25, M = 60–75;
15% BSA solution: R = 8–10, M = 70–80.

EXAMPLE 13

The purpose of this experiment was to compare human serum albumin (HSA), bovine serum albumin (BSA) and ovalbumin (OVA) as materials for converting a suspending vehicle (Tyrode solution) into a contacting media.

The starting semen sample (control) was clean (2.4 ml.) with good motility (70% – 3° motility) and semen count ($750 \times 10^6$).

The HSA (albumin (human) cryst. B grade Lot 300401, Calbiochem) and OVA (egg albumin-cryst. soluble, Lot 582367, Difco) and BSA were made up at 15% conc. in Tyrode solutions at pH 7.6. Separate 6% conc. samples of each were prepared by dilution with Tyrode solution.

In columns prepared by sealing the ends of pipettes, were added 0.5 ml. of one only of a 15% solution of HSA, BSA and OVA, respectively, (three columns of each solution, a total of 9 columns). Over the top of these solutions was layered 1.0 ml. of a corresponding 6% solution of one only of HSA, BSA and OVA, respectively. On top of each of the resulting 2-layer columns of contacting media was layered 0.5 ml ($50 \times 10^6$) of sperm suspended in Tyrode solution which had been separated from the non-sperm components in a conventional manner.

After one hour the sperm layer was carefully removed. After 1.5 hours the upper and lower layers of contacting media were separated. Initially and three hours later at room temperature, sperm counts and motility of each were determined, with the following scale of 0–4.

| Degree of Motility | | Type of Motility |
|---|---|---|
| 0° | = | No motility - at most only tail movements without forward progression |
| 1° | = | 20% or less showing progression (generally sluggish swimming movements) |
| 2° | = | 20 to 50% showing progression (generally good progressive swimming movements) |
| 3° | = | 50–80% showing progression (usually rapid swimming movements) |
| 4° | = | 80% and higher showing progression (usually very rapid swimming movements) |

A plus (+) following a number means the percentage is nearer the upper than the lower limit of the percentage range.

The results of the fraction are set forth in the table below:

| Fraction | % Motile | Motility Degree | Sperm $\times 10^6$ | % Recovery |
|---|---|---|---|---|
| Control (Starting Semen) | 61 | 3 (initial) | 150 | — |
| | 53 | 2+ (after 3 hrs) | | |
| Top | 52 | 3 | 86 | 57 |
| | (50)* | (3)* | | |
| 6% BSA | 89 | 3+ | 30 | 20 |
| | (53) | (3) | | |
| 15% BSA | 97 | 4 | 18 | 12 |
| | (79) | (4) | | 89 |
| Top | 57 | 3 | 84 | 56 |
| | (54) | (3) | | |
| 6% HSA | 65 | 3+ | 38 | 25 |
| | (50) | (3) | | |
| 15% HSA | 97 | 4 | 24 | 16 |
| | (93) | (4) | | 97 |
| Top | 54 | 3 | 87 | 58 |
| | (52) | (3) | | |
| 6% OVA | 88 | 3+ | 30 | 20 |
| | (72) | (3+) | | |
| 15% OVA | 98 | 4 | 22 | 15 |
| | (98) | (4+) | | 93 |

*recheck after 3 hours

As the data show, HSA, BSA and OVA solutions function equally well as contacting media. Whereas the % motile sperm in the unfractionated sperm had dropped to 53% with a motility degree of 2+, the sperm fractions which migrated to the 6% and 15% serum solutions initially all had substantially higher percentages of motile sperm.

Dramatic improvements in motility are achieved with marginally fertile sperm in the same manner.

EXAMPLE 14

The purpose of this experiment was to determine the extent to which the quality of stored human sperm, whose motility is far lower than that of the fresh ejaculate, is improved by the fractionation process of this invention.

A 1.0 ml. sample of sperm (initial motility: 75% – $3^{+°}$) which had been stored at cryogenic temperature (liquid nitrogen) in a conventional manner was thawed at room temperature in a water bath for five minutes. The thawed sample had a motility of 35% $2^{+°}$ (total count: $102 \times 10^6$).

To each of three columns made from pipettes with sealed ends was added 0.5 ml. of 15% BSA in Tyrode solution, which was overlayed with 1.0 ml. of 6% BSA in Tyrode solution, which was overlayed with 0.5 ml. of a suspension of the thawed sperm in Tyrode solution (count: $34 \times 10^6$). After one hour, the sperm layer was carefully removed and after 1.5 hours the BSA fractions were separated. The sperm motility of each was determined. The results are shown below:

| Fraction | Sperm Motility | |
|---|---|---|
| Thawed Sample | 35% | $2^{+°}$ |
| Top Sperm Layer | 10% | $1^{+°}$ |
| 6% BSA Layer | 70% | 3° |
| 15% BSA Layer | 85% | 4° |

It is evident from this data that the immotile sperm were separated efficiently, yielding highly motile fractions.

Comparable results are obtained with stored samples of each of bovine, equine, porcine and ovine sperms

ISOLATION KIT

Items included in the Y-sperm isolation kit are (I) 50 ml. plastic tube with screw cap for semen sample; (II) 12 ml. plastic graduated centrifuge tubes; (III) Pasteur pipettes with ends heat-sealed at point of tapering to be used as columns for Y-sperm isolation; (IV) plastic stand to place columns in vertical position; (V) disposable plastic measuring pipettes; (VI) microscope slides and cover slips; (VII) Pasteur pipettes with rubber bulb; (VIII) sterile 25% serum albumin in Tyrode buffer in a sealed vial; (IX) sterile Tyrode solution pH 7.6 in sealed vial; (X) syringe for artificial insemination.

Items are packaged and come with a set of instructions. Color coding of important steps is a possibility.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for increasing the proportion of Y-sperm in mammalian sperm, which comprises the steps of a) maintaining at least the sperm portion of progressively motile sperm-containing semen, either as such or suspended in an aqueous suspending vehicle physiologically acceptable to the sperm, as an upper layer in vertical interfacial contact, at a temperature at which the motile sperm are motile, with a lower discrete layer of a first aqueous contacting medium physiologically acceptable to the sperm and in which the motile sperm migrate downwardly at a slower rate than in the upper layer, until a portion only of the motile sperm of the semen having migrated downwardly into the contacting medium, thereby producing a contacting medium containing a higher proportion of Y to X sperm than in the starting sperm, and b) repeating the step at least once, employing in the upper layer the motile sperm which have migrated to the first aqueous contacting medium and as the lower layer a second aqueous contacting medium physiologically acceptable to the sperm and in which the motile sperm migrate downwardly at a slower rate than in the first contacting medium.

2. A process according to claim 1 wherein the sperm is human sperm.

3. A process according to claim 1 wherein the sperm is bovine sperm.

4. A process according to claim 1 wherein the sperm is porcine sperm.

5. A process according to claim 1 wherein the starting sperm is separate from the other components of the semen.

6. A process according to claim 1 wherein the starting sperm is suspended in an aqueous suspending vehicle physiologically acceptable to the sperm which does not retard the downward migration rate of the motile sperm.

7. A process according to claim 6 wherein the starting sperm is suspended in Tyrode solution.

8. A process according to claim 1 wherein the contacting medium comprises a serum albumin, ovalbumin or a serum globulin.

9. A process according to claim 8 wherein the contacting medium is a 3–25% solution of bovine serum albumin in Tyrode solution.

10. A process according to claim 1 wherein in each step the sperm layer is contacted at about room temperature with the contacting medium for about 0.5 to 10 hours.

11. A process according to claim 10 wherein the sperm is contacted with the first contacting medium for about 1 to 3 hours.

12. A process according to claim 1 wherein the second contacting medium is positioned below the first contacting medium while the latter is positioned below the starting sperm layer.

13. A process according to claim 12 wherein the starting sperm is separate from the other components of semen and is suspended in an aqueous suspending vehicle physiologically acceptable to the sperm which does not retard the downward migration rate of the sperm.

14. A process according to claim 13 wherein the sperm is human sperm.

15. A process according to claim 12 wherein the starting sperm layer is separated from the first contacting medium before the second contacting step is completed.

16. A process according to claim 1 wherein the sperm which migrates to the first contacting medium is separated therefrom and suspended in an aqueous suspending vehicle physiologically acceptable to the sperm which does not retard the downward migration rate of the motile sperm before being contacted with the second contacting medium.

17. A process according to claim 16 wherein the starting sperm is separate from the other components of semen and is suspended in an aqueous suspending vehicle physiologically acceptable to the sperm which does not ratard the downward migration rate of the sperm.

18. A process according to claim 17 wherein the sperm is human sperm.

19. A process according to claim 1 wherein after motile sperms have migrated into the first contacting medium the latter is separated from the starting sperm layer and thereafter contacted with the second contacting medium.

20. A process according to claim 19 wherein the starting sperm is separate from the other components of semen and is suspended in an aqueous suspending vehicle physiologically acceptable to the sperm which does not retard the downward migration rate of the sperm.

21. A process according to claim 20 wherein the sperm is human sperm.

22. A process for increasing the proportion of motile to immotile sperm in mammalian sperm, which comprises the steps of a) separating the sperm from the other components of the semen; b) suspending the separated sperm portion of the semen in an aqueous suspending vehicle physiologically acceptable to the sperm and which does not substantially retard the downward migration rate of motile sperm; c) maintaining the sperm-containing suspending vehicle as an upper layer in interfacial contact, at a temperature at which the motile sperm are motile, with a lower discrete layer of an aqueous contacting medium which is physiologically acceptable to the sperm and in which the motile sperm migrate downwardly at a slower rate than in the suspending vehicle, until at least a portion of the motile sperm of the separated sperm have migrated downwardly into the contacting medium, thereby producing a sperm fraction having a higher proportion of motile sperm than in the starting sperm; and d) thereafter separating the contacting medium, containing the motile sperm enhanced fraction of the starting sperm, from the suspending vehicle layer.

23. A process according to claim 22 wherein the sperm is human sperm.

24. A process according to claim 22 wherein the sperm is bovine sperm.

25. A process according to claim 22 wherein the sperm is equine sperm.

26. A process according to claim 22 wherein the motile sperm which migrate to the contacting medium are thereafter separated therefrom.

27. A process according to claim 22 wherein the starting sperm is suspended in Tyrode solution.

28. A process according to claim 22 wherein the contacting medium comprises a serum albumin, ovalbumin or a serum globulin.

29. A process according to claim 28 wherein the contacting medium is a 3–25% solution of bovine serum albumin in Tyrode solution.

30. In a method for artificially inseminating a mammalian female, the improvement which comprises employing motile sperm enriched sperm obtained according to the process of claim 22.

31. A method according to claim 30 wherein the mammal is a human.

32. A method according to claim 30 wherein the mammal is a bovine.

33. A method according to claim 30 wherein the mammal is an equine.

34. A method for increasing the incidence of males in mammalian offspring which comprises artificially inseminating a fertile female with Y-sperm enriched sperms of the same species of mammal obtained according to the process of claim 1.

35. A method according to claim 34 wherein the mammal is human.

36. A method according to claim 34 wherein the mammal is bovine.

37. A method according to claim 34 wherein the mammal is porcine.

* * * * *